United States Patent
Panicheva et al.

(10) Patent No.: US 11,452,778 B2
(45) Date of Patent: Sep. 27, 2022

(54) STABILIZED HYPOHALOUS ACID SOLUTIONS

(71) Applicant: URGO US, INC., Fort Worth, TX (US)

(72) Inventors: Svetlana Panicheva, Downingtown, PA (US); Mark N. Sampson, Doylestown, PA (US); Vadim Panichev, Downingtown, PA (US); Gerald N. DiBello, West Chester, PA (US)

(73) Assignee: URGO US, INC., Fort Worth, TX (US)

( * ) Notice: Subject to any disclaimer, the term of this patent is extended or adjusted under 35 U.S.C. 154(b) by 0 days.

(21) Appl. No.: 16/737,671

(22) Filed: Jan. 8, 2020

(65) Prior Publication Data

US 2020/0138953 A1    May 7, 2020

Related U.S. Application Data

(63) Continuation-in-part of application No. 16/018,306, filed on Jun. 26, 2018, now Pat. No. 10,576,152, which is a continuation of application No. 15/184,207, filed on Jun. 16, 2016, now Pat. No. 10,034,942, which is a continuation of application No. 14/501,977, filed on Sep. 30, 2014, now Pat. No. 9,392,787, which is a continuation of application No. 13/423,822, filed on Mar. 19, 2012, now Pat. No. 8,871,278.

(60) Provisional application No. 61/526,149, filed on Aug. 22, 2011, provisional application No. 61/454,383, filed on Mar. 18, 2011.

(51) Int. Cl.

| | |
|---|---|
| C02F 1/461 | (2006.01) |
| A01N 25/22 | (2006.01) |
| C25B 1/00 | (2021.01) |
| A61K 33/10 | (2006.01) |
| A61K 33/22 | (2006.01) |
| A61K 47/02 | (2006.01) |
| C01B 11/04 | (2006.01) |
| A23L 3/358 | (2006.01) |
| A01N 59/00 | (2006.01) |
| A61K 33/42 | (2006.01) |
| A61K 33/14 | (2006.01) |
| A61K 33/12 | (2006.01) |
| A61K 33/20 | (2006.01) |

(52) U.S. Cl.
CPC ............ *A61K 47/02* (2013.01); *A01N 25/22* (2013.01); *A01N 59/00* (2013.01); *A23L 3/358* (2013.01); *A61K 33/10* (2013.01); *A61K 33/12* (2013.01); *A61K 33/14* (2013.01); *A61K 33/20* (2013.01); *A61K 33/42* (2013.01); *C01B 11/04* (2013.01)

(58) Field of Classification Search
CPC ........ A01N 59/00; A01N 25/04; A01N 59/14; A01N 25/00; A01N 59/08; A01N 25/22; A01N 25/02; C02F 1/76; C02F 1/4674; C02F 1/467; C01B 7/09; C01B 9/04; A61K 2300/00; A61K 33/20; A61K 31/02; A61K 31/327; A61K 33/10; A61K 33/22; A61L 2/035; A61L 2/18; A61L 2/0088

See application file for complete search history.

(56) References Cited

U.S. PATENT DOCUMENTS

| | | |
|---|---|---|
| 4,048,300 A | 9/1977 | Tomliinson et al. |
| 4,051,055 A | 9/1977 | Trinh et al. |
| 4,104,190 A | 8/1978 | Hartshorn |
| 4,507,285 A | 3/1985 | Kuhne |
| 4,859,513 A | 8/1989 | Gibbons et al. |
| 5,424,079 A * | 6/1995 | Yu .......................... A01N 55/08 210/754 |
| 5,427,667 A | 6/1995 | Bakhir et al. |
| 5,731,008 A | 3/1998 | Morrow |
| 6,022,840 A | 2/2000 | Weibel |
| 6,036,789 A | 3/2000 | Weibel |
| 6,313,082 B1 | 11/2001 | Scialla et al. |
| 6,333,054 B1 | 12/2001 | Rogozinski |
| 6,426,066 B1 | 7/2002 | Najafi et al. |
| 6,927,192 B2 | 8/2005 | Martinelli et al. |
| 7,276,255 B2 | 10/2007 | Selkon |
| 7,393,522 B2 | 7/2008 | Najafi et al. |
| 7,517,568 B2 | 4/2009 | Bitowft et al. |
| 7,527,783 B2 | 5/2009 | Shaheen et al. |
| 8,147,444 B2 | 4/2012 | Alimi et al. |
| 8,871,278 B2 | 10/2014 | Panicheva et al. |

(Continued)

FOREIGN PATENT DOCUMENTS

| | | |
|---|---|---|
| EP | 0867501 A1 | 9/1998 |
| EP | 1323678 A1 | 7/2003 |

(Continued)

OTHER PUBLICATIONS

Chlorination Chemistry, Mountain Empire Community College, http://water.me.vccs.edu/concepts/chlorchemistry.html (Nov. 16, 2004).
MIT OpenCourseWare, 3.091SC Introduction to Solid State Chemistry, http://ocw.mit.edu (Fall, 2009).
International Search Report and Written Opinion from PCT Application No. PCT/US2012/029650, 10 pages (dated Jun. 19, 2012).
European Search Report, EP12760461, dated Apr. 8, 2015, 5 pages.

*Primary Examiner* — Tracy Liu
(74) *Attorney, Agent, or Firm* — Morgan, Lewis & Bockius LLP

(57) ABSTRACT

The present invention provides a stabilized hypohalous acid solution (or formulation thereof), which may be conveniently packaged for sale, or stored for later use on demand. The invention further provides methods of making the stabilized hypohalous acid solution, as well as methods of use for disinfecting mammalian tissue, including wounds and burns, disinfecting or cleansing surfaces, or treating and/or preserving food products and cut flowers, among other uses.

13 Claims, 12 Drawing Sheets

(56) References Cited

U.S. PATENT DOCUMENTS

| | | |
|---|---|---|
| 2002/0071805 A1 | 6/2002 | Khan et al. |
| 2002/0110602 A1 | 8/2002 | Sorenson |
| 2002/0160053 A1 | 10/2002 | Yahagi et al. |
| 2002/0172725 A1* | 11/2002 | Zolotarsky ............. A01N 59/00 424/688 |
| 2003/0109398 A1 | 6/2003 | Yoneda et al. |
| 2003/0141202 A1 | 7/2003 | Nakamura et al. |
| 2003/0146108 A1 | 8/2003 | Nakamura et al. |
| 2003/0180385 A1 | 9/2003 | Martinelli et al. |
| 2003/0185704 A1 | 10/2003 | Bernard et al. |
| 2004/0072712 A1 | 4/2004 | Man et al. |
| 2004/0137078 A1 | 7/2004 | Najafi et al. |
| 2004/0256330 A1 | 12/2004 | Okazaki |
| 2005/0139808 A1 | 6/2005 | Alimi |
| 2005/0142157 A1 | 6/2005 | Alimi |
| 2005/0196462 A1 | 9/2005 | Alimi |
| 2005/0214386 A1 | 9/2005 | Shaheen et al. |
| 2006/0235350 A1 | 10/2006 | Alimi et al. |
| 2006/0241002 A1 | 10/2006 | Rogozinski |
| 2006/0241546 A1 | 10/2006 | Alimi |
| 2006/0253060 A1 | 11/2006 | Alimi |
| 2007/0108064 A1 | 5/2007 | Buckley et al. |
| 2007/0196357 A1 | 8/2007 | Alimi et al. |
| 2007/0196434 A1 | 8/2007 | Alimi et al. |
| 2007/0231247 A1 | 10/2007 | Bromberg et al. |
| 2008/0014289 A1 | 1/2008 | Li |
| 2008/0160612 A1 | 7/2008 | Selkon |
| 2009/0092685 A1 | 4/2009 | Selkon |
| 2009/0110749 A1 | 4/2009 | Norton et al. |
| 2009/0148342 A1 | 6/2009 | Bromberg et al. |
| 2009/0169646 A1 | 7/2009 | Bosch et al. |
| 2009/0221989 A1 | 9/2009 | Najafi et al. |
| 2009/0305888 A1 | 12/2009 | Li et al. |
| 2010/0030132 A1 | 2/2010 | Niezgoda et al. |
| 2010/0092399 A1 | 4/2010 | Alimi et al. |
| 2010/0183745 A1 | 7/2010 | Rossi et al. |
| 2010/0285151 A1 | 11/2010 | Goldan et al. |
| 2010/0310672 A1 | 12/2010 | Beltrup et al. |
| 2011/0020474 A1 | 1/2011 | Najafi et al. |
| 2011/0028319 A1 | 2/2011 | Panicheva et al. |
| 2012/0024028 A1 | 2/2012 | Panicheva et al. |
| 2012/0156307 A1 | 6/2012 | Chen et al. |
| 2012/0164235 A1 | 6/2012 | Northey |
| 2012/0269904 A1* | 10/2012 | Northey ................. A01N 59/00 424/661 |
| 2013/0028990 A1 | 1/2013 | Smith et al. |
| 2015/0231173 A1 | 8/2015 | Sampson et al. |

FOREIGN PATENT DOCUMENTS

| | | |
|---|---|---|
| EP | 0867502 B1 | 11/2004 |
| EP | 1259114 B1 | 12/2004 |
| EP | 1550468 B1 | 4/2007 |
| EP | 1969938 A2 | 9/2008 |
| EP | 2100602 A1 | 12/2008 |
| EP | 2241322 A1 | 10/2010 |
| EP | 2146580 B1 | 10/2011 |
| JP | S50003419 | 2/1974 |
| JP | 2002167301 | 6/2002 |
| JP | 2003-286130 | 10/2003 |
| JP | 2005000238 | 1/2005 |
| JP | 2005245964 | 9/2005 |
| JP | 2008255310 | 10/2006 |
| JP | 2007530731 | 11/2007 |
| JP | 2009-161453 | 7/2009 |
| JP | 3166522 | 2/2011 |
| WO | 9209291 | 6/1992 |
| WO | 199602271 A1 | 1/1996 |
| WO | 1997031095 | 8/1997 |
| WO | 1999034652 | 7/1999 |
| WO | 1999059924 | 11/1999 |
| WO | 2003040038 | 5/2003 |
| WO | 2005049779 | 6/2005 |
| WO | 2005094439 A2 | 10/2005 |
| WO | 2005113026 A2 | 12/2005 |
| WO | 2005117914 A2 | 12/2005 |
| WO | 2006014223 A1 | 2/2006 |
| WO | 2006057311 A1 | 6/2006 |
| WO | 2007070637 A2 | 6/2007 |
| WO | 2007072697 A1 | 6/2007 |
| WO | 2007075865 | 7/2007 |
| WO | 2008072388 A1 | 6/2008 |
| WO | 2008089268 A2 | 7/2008 |
| WO | 2008089893 A1 | 7/2008 |
| WO | 2008099471 A1 | 8/2008 |
| WO | 2008112940 A1 | 9/2008 |
| WO | 2009098870 A | 8/2009 |
| WO | 2009098873 A | 8/2009 |
| WO | 2010027825 A2 | 3/2010 |
| WO | 2010090361 A1 | 8/2010 |
| WO | 2010146460 A1 | 12/2010 |
| WO | 2011014809 | 2/2011 |
| WO | 2011058764 A1 | 5/2011 |
| WO | 2011090376 A1 | 7/2011 |
| WO | 2011161518 A2 | 12/2011 |
| WO | 2012062461 | 5/2012 |
| WO | 2012129161 | 9/2012 |
| WO | 2012150477 A2 | 11/2012 |

* cited by examiner

STABILIZED HYPOHALOUS ACID SOLUTIONS

RELATED APPLICATIONS

This application is a continuation-in-part of U.S. patent application Ser. No. 16/018,306 filed Jun. 26, 2018, which is a continuation of U.S. patent application Ser. No. 15/184,207 filed Jun. 16, 2016 (U.S. Pat. No. 10,034,942), which is a continuation of U.S. patent application Ser. No. 14/501,977 filed Sep. 30, 2014 (U.S. Pat. No. 9,392,787), which is a continuation of U.S. patent application Ser. No. 13/423,822 filed Mar. 19, 2012 (U.S. Pat. No. 8,871,278), which claims the benefit of and priority to U.S. Provisional Application No. 61/454,383, filed Mar. 18, 2011, and U.S. Provisional Application No. 61/526,149, filed Aug. 22, 2011, each of which is hereby incorporated by reference in its entirety.

TECHNICAL FIELD

The present invention relates to stabilized solutions and formulations of hypohalous acid, such as hypochlorous acid (HOCl), as well as methods for their production and use. The solution finds use for cleaning and/or disinfecting surfaces, food such as fruit, vegetables and crops, or mammalian tissues (including wounds). The solutions further find use in the preservation of agricultural products and cut flowers.

BACKGROUND

Hypochlorous acid is an oxidant and biocide that is produced by the human body's natural immune system to fight infection. Hypochlorous acid is generated as the final step of the Oxidative Burst Pathway, with large quantities of hypochlorous acid being released into the phagocytic vesicles to destroy the invading microorganisms. It is considered that hypochlorous acid exerts its biocidal effect by attacking the surface and plasma membrane proteins, impairing transport of solutes and the salt balance of bacterial cells (Pieterson et al., Water SA, 22(1): 43-48 (1996)). Escherichia coli exposed to hypochlorous acid lose viability in less than 100 ms due to inactivation of many vital systems. (Fair et al., 40 J. Am. Water Works Assoc. 1051-61 (1940)). Hypochlorous acid at 2.6 ppm caused 100% growth inhibition of E. coli in dilute bacterial suspensions in about 5 minutes. (Chesney et al., 178 J. Bacteria 2131-2135 (1996)). According to Chemistry of Water Treatment ($2^{nd}$ Edition), S. D. Faust and O. M. Aly (1998), 100% kill in 5 minutes requires only 0.08 ppm for A. aerogenes, 0.06 ppm for S. typhosa, 0.05 ppm for S. dysenteriae, and 0.03 ppm for E. coli.

Although hypochlorous acid is biocidal for microorganisms, it is not significantly toxic to human or animal cells, at least partly because human and animal cells have extensive, highly effective defense mechanisms known as the Antioxidant Defense System (ADS).

Hypohalous acid has a wide range of applications where it is important to control microbial contamination, such as for the care and management of wounds, disinfecting hard surfaces such as medical or dental equipment, food safety and processing, water treatment, as well as other industrial and agricultural applications.

One limitation associated with solutions of hypochlorous acid is their stability, which has limited much of the commercial use to those situations where the solution can be made on site for relatively immediate use. Existing alternatives include Dakin's solution for wound care, which is a diluted sodium hypochlorite solution (0.5%) prepared by mixing sodium hypochlorite (5.25%), sodium bicarbonate/carbonate (1%), and clean tap water. However, Dakin's solution has a high pH, and thus causes pain and burning in wound treatment along with rashes, itching, swelling, hives, and/or blisters. Further, Dakin's solution is unstable and unsuited for clinical use at lower pH's (<8.5). Another alternative is the Microcyn™ solution. While Microcyn has a 2 year shelf life, it suffers from a limited level of available free chlorine (AFC) of about 80 ppm (pH of 7.4), and lower percent of hypochlorous acid, which may limit its biocidal effectiveness. EcaFlo™ is available for hard surface disinfection. This solution contains equimolar amounts of hypochlorite and hypochlorous acid in addition to high sodium chloride content. The pH of the solution is around 7.5 and the solution has an AFC content of approximately 460 ppm. The solution has a relatively short shelf life of 30 days.

There is an unmet need for a hypohalous acid solution that has a high AFC content, has sufficient stability and/or other properties required to be commercially useful in medical and other commercial settings, and is not irritating or harmful to humans. The claimed invention meets these and other objectives.

SUMMARY OF THE INVENTION

The present invention provides a stabilized hypohalous acid solution or formulation thereof, which may be conveniently packaged for sale, or stored for later use on demand. The invention further provides methods of making the stabilized hypohalous acid solution or formulation thereof, as well as methods of use for disinfecting mammalian tissue, including wounds and burns, disinfecting or cleansing hard surfaces, treating (e.g., preserving and/or disinfecting) food products or cut flowers, among other uses.

In one aspect, the invention provides a stabilized hypohalous acid solution, which can be a hypochlorous acid solution or a hypobromous acid solution for example. The solution incorporates a stabilizing amount of dissolved inorganic carbon (DIC), which can be in the form of a bicarbonate or carbonate of an alkali or alkaline earth metal. The solution may have an available free chlorine (AFC) content of from about 10 to about 10,000 parts per million, and a pH of from about 4.0 to about 7.5. For example, in certain embodiments, the solution has a pH of from about 5 to about 7. In certain embodiments, the solution contains hypochlorous acid, and is prepared by electrolysis of saline. The solution is stabilized, as determined by its change in pH and/or AFC over time, for at least one month, but in various embodiments, the solution is stabilized for at least six months, at least one year, or more.

In certain embodiments, sodium bicarbonate is incorporated into the solution at a level of about 5:1 to about 1:5 molar ratio relative to the AFC content. For example, sodium bicarbonate may be added at a level of about 1:1, about 1:2, or about 1:3 or at a larger (i.e., more dilute) molar ratio relative to the AFC content (e.g., the hypohalous acid content). In certain embodiment, sodium bicarbonate is incorporated into the solution at a level of about 1:1 to about 1:2, relative to the AFC content. While the solution may contain phosphate buffers in some embodiments, in other embodiments, the solution does not contain, or contains only limited, phosphate buffer. For example, the solution may comprise HOCl produced by electrolysis of saline, and the solution may have an AFC content of from about 100 to about 500 parts per million, a pH in the range of about 5 to about 7, a salinity of about 0.02% to about 1.0%, and an amount of dissolved inorganic carbon in the range of about 300 mg/L to about 1500 mg/L. In some embodiments, the salinity of the solution does not impact the amount of bicarbonate needed for solution stabilization. In certain embodiments, the HOCl solution is formulated as a hydrogel.

In another aspect, the invention provides a method for preparing the stabilized hypohalous acid solution. The method involves incorporating the DIC (e.g., in the form of carbonate or bicarbonate) by addition to an electrolyte for electrochemical treatment, or incorporating the DIC (e.g., in the form of carbonate or bicarbonate) by directly adding to an electrolyzed solution comprising hypohalous acid (e.g., HOCl).

Still other aspects of the invention provide methods of disinfecting, cleansing, or treating a mammalian tissue, such as a wound, burn, or dermatosis, or provides methods of sanitizing, disinfecting or cleansing a hard surface, or provides methods for treating or preserving a food or agricultural product or cut flowers. Due to the stability of the hypohalous acid solutions and formulations, such methods need not be performed proximately to the production of the biocidal solution. Further, as shown herein, stabilized hypohalous acid solutions of the invention maintain activity even in the presence of high organic load. In still other embodiments, the invention provides a method for treating a skin condition, including dermatosis, rosasea, skin infection, skin allergy, psoriasis, or acne. In such embodiments, the HOCl may be formulated as a hydrogel.

Other aspects of the invention will be apparent from the following detailed description of the invention.

DESCRIPTION OF THE FIGURES

(FIG. 1B).

(FIG. 2B).

FIG. 7A shows stability of pH. FIG. 7B shows stability of AFC content.

DETAILED DESCRIPTION

Figure 1A:
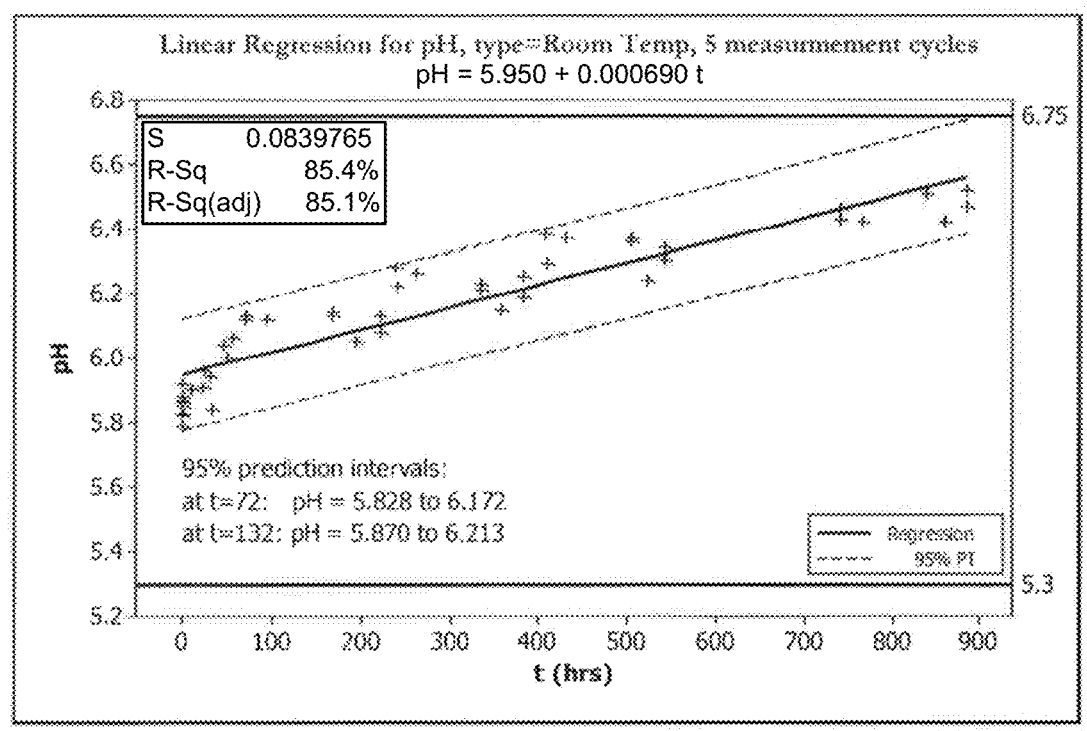
FIGS. 1A and 1B show the change in pH over time of an HOCl solution stored at room temperature (FIG. 1A) or stored at less than 20° C.
Figure 1B:
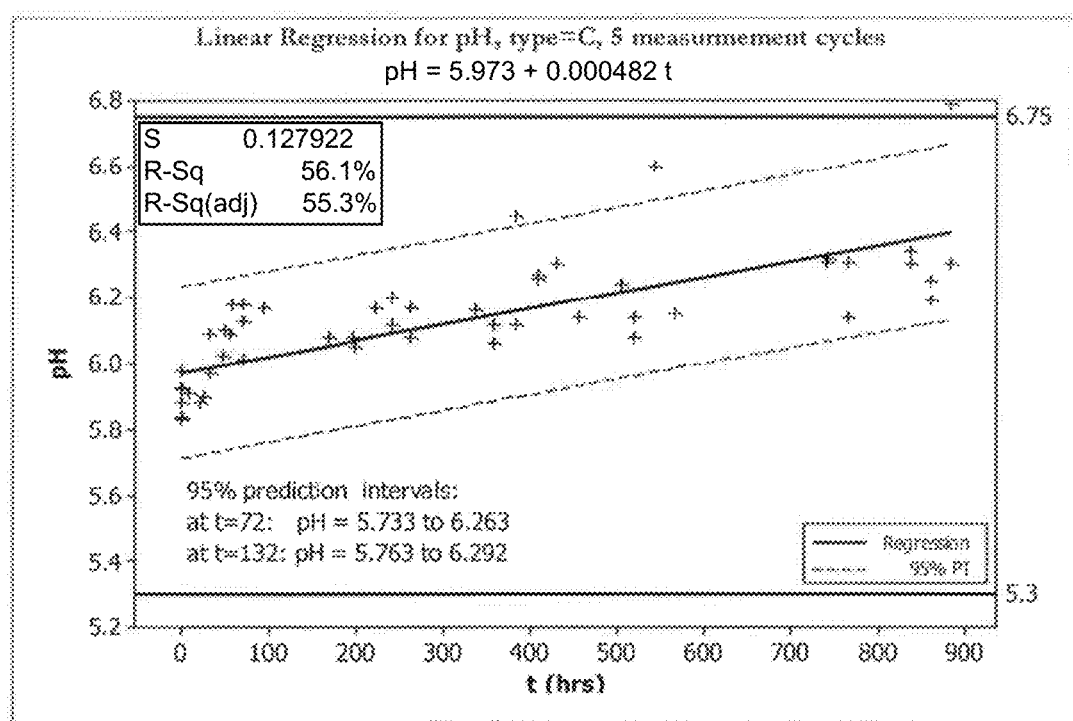
Figure 2A:
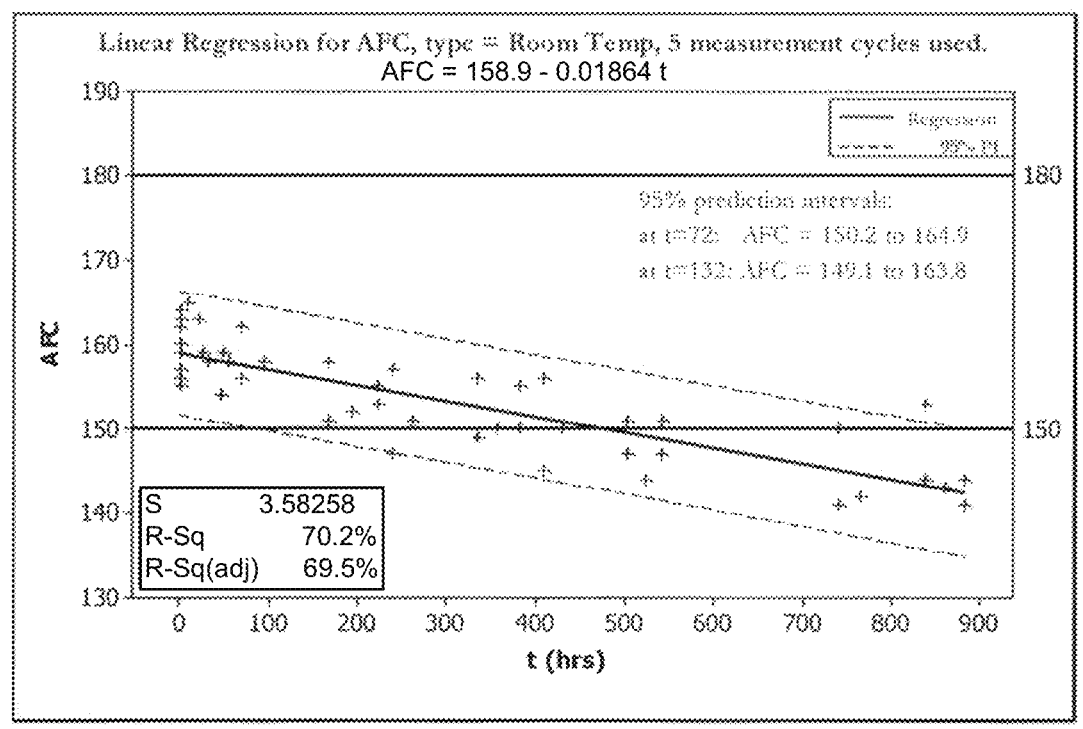
FIGS. 2A and 2B show the change in AFC over time of an HOCl solution stored at room temperature (FIG. 2A) or stored at less than 20° C.
Figure 2B:
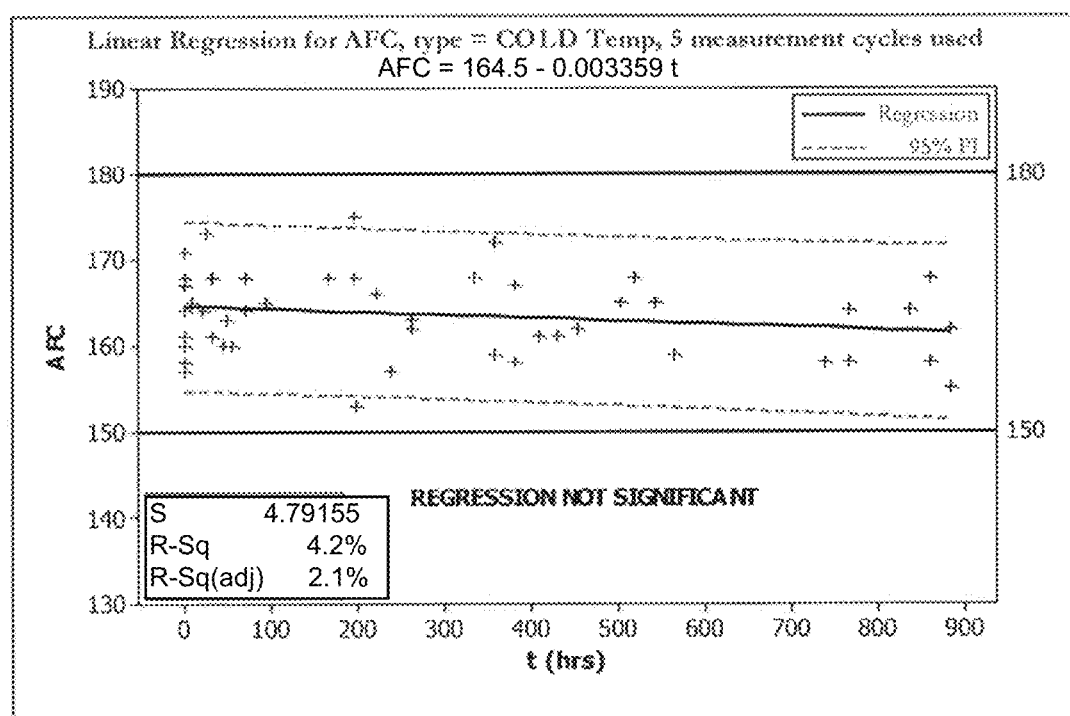

The present invention provides a stabilized hypohalous acid solution or formulation thereof, which may be conveniently packaged for sale, or stored for later use on demand. The invention further provides methods of making the stabilized hypohalous acid solution, as well as methods of use for disinfecting mammalian tissue, including wounds and burns, disinfecting or cleansing surfaces, or treating or preserving food products or cut flowers, among other uses.

In one aspect, the invention provides a stabilized hypohalous acid solution or formulation thereof, which can be a hypochlorous acid solution or formulation or a hypobromous acid solution or formulation, for example. The solution incorporates a stabilizing amount of dissolved inorganic carbon (DIC), such as a bicarbonate or carbonate of an alkali or alkaline earth metal. The solution may have an available free chlorine (AFC) content of from about 10 to about 10,000 parts per million, and a pH of from about 4.0 to about 7.5. In certain embodiments, the solution contains hypochlorous acid, and is prepared by electrolysis of saline. The solution is stabilized, as determined by its change in pH and/or AFC over time, for at least one month, but in various embodiments, the solution is stabilized for at least six months, at least one year, or more.

The hypohalous acid solution may be generated by electrolysis of a halide salt, such as chloride salt (e.g., sodium chloride) or a bromide salt, and may comprise a mixture of oxidizing species such as, e.g., predominantly hypochlorous acid and sodium hypochlorite, or hypobromous acid and sodium hypobromite. Hypochlorous acid and hypochlorite (or hypobromous acid and hypobromite) are in equilibrium and the position of the equilibrium is determined predominately by the pH (that is, pH effects the concentration of each component). An electrolyzed sodium chloride solution with a pH of 5.1 to 6.0 has a purity of about ≥95% hypochlorous acid. Thus, the electrolyzed solution supplied may have a pH of from about 4.0 to about 7.5, but in certain embodiments has a pH of from about 4.4 to about 7.0, or a pH of about 5 to about 7, or a pH of from about 5.4 to about 6.4, or a pH of from about 5.0 to about 6.4. At a pH of about 5.4 the solution will contain mostly (close to 100%) hypochlorous acid with respect to hypochlorite.

While the solution may comprise, or consist essentially of hypochlorous acid as the active agent, in some embodiments, it may contain other hypohalous acids (e.g., HOBr, or mixture thereof). In some embodiments, the solution contains other oxidizing or radical producing species such as a hypohalite (e.g., hypochlorite), hydroxide, $H_2O_2$ and $O_3$, among others. The present invention relates to stabilized hypohalous acids, such as hypochlorous acid or hypobromous acid. While the specification refers to Available Free Chlorine when referring to the concentration of the hypohalous acid (for convenience), a person of skill in the art understands that, in the case of hypobromous acid, the hypohalous acid concentration can be referred to as AFB (available free bromine).

The biocidal activity of the solution can be expressed in terms of available free chlorine or AFC. While the invention is applicable to an AFC range of from about 10 to about 10,000 ppm (or to about 5000 ppm), in certain embodiments, the solution has a relatively high AFC content and is suitable for use with mammalian tissues or agricultural products. For example, the solution may have an AFC content of from about 100 to 1000 ppm, or 100 to 500 ppm, or about 150 to about 250 ppm. Other AFC levels may be employed, and may be selected based upon the intended application. For example, without any limitation, for surface disinfection the AFC may be in the range of about 140 to about 2000 ppm, or about 400 to about 1000 ppm.

While the hypochlorous acid may be produced chemically in accordance with some embodiments (e.g., by acidification of hypochlorite), the hypohalous acid may also be produced electrochemically. The electrochemical production of hypohalous acid is by treatment of halide-based electrolytes in a diaphragm-type electrolytic cell. Electrochemical treatment of saline is described, for example, in U.S. Pat. Nos. 7,303,660, 7,828,942, and 7,897,023, which are hereby incorporated by reference in their entireties.

The solution employs a stabilizing amount of DIC, which may be a bicarbonate or carbonate of alkali or alkaline earth metal, such as, for example, sodium, potassium, calcium, or magnesium. In some embodiments, the bicarbonates or carbonates are added prior to the formation of hypohalous acid (e.g., by electrochemical treatment), and in other embodiments, the bicarbonates or carbonates are added to the solution after formation of hypohalous acid. For example, the bicarbonate(s) or carbonate(s) may be added to the precursor solution, the electrolyte, and/or the end solution.

The DIC is incorporated at a "stabilizing amount," which can be determined with reference to the change in the pH or AFC content of the solution over time. Generally, the solution is considered stabilized if the amount of AFC does not drop below about 75% of the initial value over a period of about 6 months. In certain embodiments, the AFC content is stabilized for at least one year from the production date of the solution. Further, the stability of the solution may be determined with reference to the pH. Generally, the solution is considered stabilized if the pH does not vary by 1 unit over a period of about 6 months. In certain embodiments, the pH is stabilized for at least one year from the production date of the solution. The solution should be stored at 25° C. or at 20° C. or less for greater stability. 25° C. and 20° C. are the reference temperatures for determination of stability. For stability testing, solutions are packaged in HDPE bottles, stored in the dark, and kept unopened.

The stabilizing amount of DIC (e.g. as added carbonate or bicarbonate) can be determined with reference to the AFC content. For example, in certain embodiments, the stabilizing amount of the carbonate or bicarbonate is incorporated into the solution at a molar ratio of from about 5:1 to 1:5 with respect to the AFC level. In some embodiments, the bicarbonates or carbonates are incorporated into the solution in at least equimolar amounts with respect to the AFC content (e.g., hypochlorous acid content). In still other embodiments, the DIC (e.g., bicarbonate or carbonate) is incorporated at about 5:1, about 2:1, about 1:1, about 1:2, about 1:3, or about 1:5 with respect to AFC content. In various embodiments, other buffering components such as phosphate buffers, are not employed, or are minimally employed. For example, for solutions having an AFC content of from about 200 ppm to about 500 ppm, carbonate or bicarbonate may be incorporated at an amount of from about 300 mg/L to about 1500 mg/L to stabilize the solution. In certain embodiments, such solutions are stabilized by incorporating from about 400 to about 1000 mg/L of carbonate or bicarbonate.

Without being bound by theory, dissolved inorganic carbon (DIC), which generally includes carbonates, bicarbonates, carbonic acid and dissolved $CO_2$, provides low or minimal buffering capacity in the pH range targeted by the solutions and compositions described herein. Nevertheless, these solutions are effectively stabilized, such that the solutions and compositions are not dependent on "on-demand" production. The stabilizing effect can be due to, in-part, free radical scavenging ability of DIC to thereby slow the decomposition of HOCl. Further still, solutions prepared by electrochemical treatment of bicarbonate-enriched sodium chloride solution (as opposed to chemical acidification of sodium hypochlorite stabilized with equal amount of carbonate/bicarbonate), have distinct properties with respect to DIC, and the stabilizing effect can be distinct.

Figure 5:
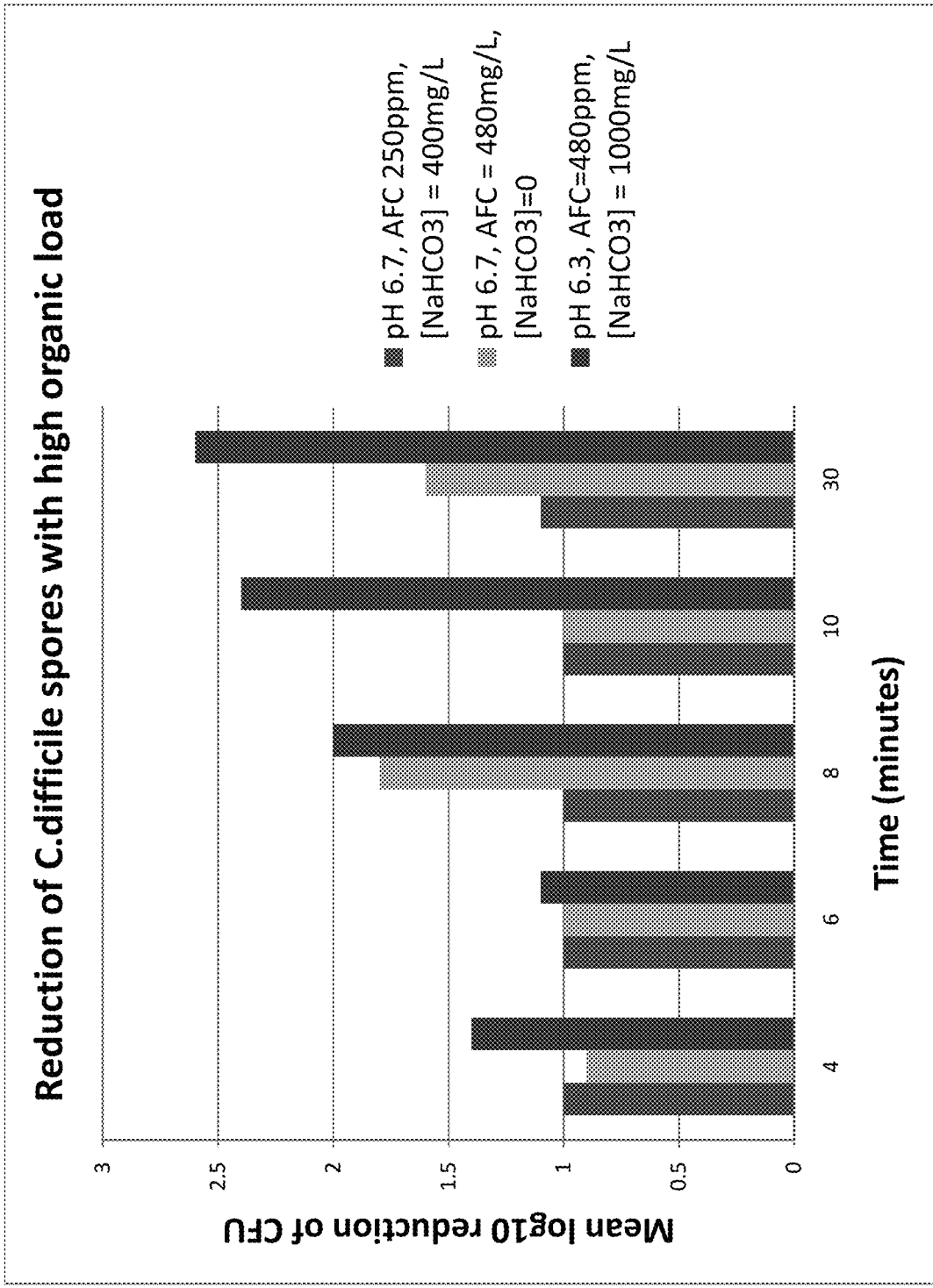
FIG. 5 shows the reduction in *C. difficile* spores in the presence of high organic load. The solutions tested are as follows: pH 6.7, AFC of 250 ppm, $NaHCO_3$ at 400 mg/L; pH 6.7, AFC of 480 mg/L, 0.0 $NaHCO_3$; and pH 6.3, AFC of 480 ppm, and $NaHCO_3$ at 1000 mg/L.

In some embodiments, as shown in FIG. 5, the addition of the bicarbonates or carbonates of alkali or alkaline earth metals provides enhanced biocidal effectiveness for treating microorganism or biofilms, especially in the presence of high organic load.

While the hypohalous acid solution may be in the form of a liquid, the solution may take the form of a cream, gel (e.g. silicon-based gel), and/or foam by the addition of conventional ingredients known in the art. For example, topical formulations of electrochemical solutions are disclosed in US 2005/0196462, which is hereby incorporated by reference in its entirety. In these embodiments, the formulation is better contained around the application site by limiting solution run-off. Further, convenient applicators for creams, foams, and the like are known, and may be used in accordance with the present invention. Since the solutions of the invention provide the potential for low conductivity, even with relatively high AFC content, and at "skin-friendly" pH levels, the solutions of the invention are particularly suitable for hydrogel formulations.

In certain embodiments employing hydrogel formulations, the composition has an AFC content of greater than about 100 ppm, greater than about 150 ppm, greater than about 200 ppm, greater than about 250 ppm, or greater than about 300 ppm. Further, the formulation may have a viscosity of from about 0.5 mS/cm to about 12 mS/cm, such as from about 1 mS/cm to about 10 mS/cm in some embodiments. Further, hydrogel formulations in some embodiments have a pH of from about 5 to about 7, or from about 5 to about 6.5 in other embodiments. The hydrogels may be prepared from silicate-based carriers, such as sodium magnesium fluorosilicate (e.g., from about 0.5% to about 5%), and may employ an additional buffer for targeting the pH. An exemplary buffer is phosphoric acid.

The stabilized solutions may be packaged for storage or sale, using any suitable container, such as any suitable plastic or glass bottles, or bags (e.g., plastic bags), tubes, or cans (e.g., spray or aerosol). In certain embodiments, the packaging material has minimal gas permeability, including by species such as $CO_2$ and $O2$. The containers may be transparent, or opaque so that they are impenetrable by light, and may be of any unit volume, such as about 100 ml, about 125 ml, about 250 ml, about 0.5 liter, about 1 liter, about 5 liters, about 10 liters, or greater.

The hypochlorous acid solution of the invention may also be hypertonic, hypotonic, or isotonic with respect to physiological fluids (blood, plasma, tears, etc.). Alternatively, the solution may contain varying levels of salinity, such as from 0.01 to about 2.0%. Generally, the solution contains from about 0.02% to about 0.9% w/v NaCl when intended for use in medicine. In some embodiments, the solution may be a normal saline solution (about 0.9% w/v NaCl). In some embodiments, the solution may contain from about 0.01 to 2.0% w/v one or more salts, such as a halide salt, e.g. NaCl, KCl, or a mixture of salts or halide salts. The salt, or halide salt may be a salt of an alkali metal or alkaline earth metal, such as sodium, potassium, calcium, or magnesium. In certain embodiments, the electrolyzed solution is generated using a mixture of physiologically balanced salts, as disclosed in U.S. Pat. No. 6,426,066, which is hereby incorporated by reference in its entirety. Such salts may include potassium halides (e.g., KCl) and magnesium halides (e.g., $MgCl_2$).

In another aspect, the invention provides a method for preparing the stabilized hypohalous acid solution. The method involves incorporating the carbonate or bicarbonate into an electrolyte for electrochemical treatment, or directly to an electrolyzed solution comprising hypohalous acid (e.g., HOCl).

For example, an electrolyzed solution or other hypohalous acid solution may be diluted with water or aqueous solution comprising bicarbonates or carbonates. In other embodiments, the diluted hypohalous acid solution (e.g., having the desired AFC content) is added to containers comprising dry bicarbonates or carbonates of alkali or alkaline earth metals. The latter is an effective method for production of low ionic strength hypohalous acid solutions, especially for hydrogel formulations.

The stabilized hypohalous acid solutions (e.g. solutions of greater than 90%, 95%, or 97% HOCl) may be obtained by electrolysis of a saline solution as described in U.S. Pat. No. 7,276,255, which is hereby incorporated by reference in its entirety, or can be prepared by any suitable method or apparatus, by incorporating the bicarbonate or carbonate into the dry electrolyte or the solution for electrolysis. The carbonate or bicarbonate can be added to the dry electrolyte in accordance with the desired AFC content of the resulting solution, as described in detail herein. Hypochlorous acid solutions may be prepared by passing saline solution containing the carbonate/bicarbonate over coated titanium electrodes separated by a semi-permeable ceramic membrane at a current of about 6 to 9 Amps. Electrochemical treatment of saline is described, for example, in U.S. Pat. Nos. 7,303,660, 7,828,942, and 7,897,023, which are hereby incorporated by reference.

Still other aspects of the invention provide methods of disinfecting or cleansing a mammalian tissue, such as a wound or burn, or disinfecting or cleansing a hard surface, or for treating or preserving a food product or cut flowers. Due to the stability of the hypohalous acid solutions, such methods need not be performed proximately to the production of the biocidal solution, and the solution may be prepared well in advance of its use.

The solutions and formulations of the invention may be used as a sterilizing, disinfecting and biocidal solution for human and animal care. The solutions are non-hazardous, non-irritating, non-sensitizing to the skin, non-irritating to the eyes, not harmful if swallowed, and show no evidence of mutagenic activity. For example, the method of the invention provides for moistening, lubricating, irrigating, cleaning, deodorizing, disinfecting, or debriding a wound by rinsing, washing or immersing the wound, with or in, the stabilized or stored hypohalous acid solutions, or by applying the solution to the wound and/or wound dressing. The wound may or may not be infected, and thus the method of the invention is useful for treating infected wounds and useful for preventing infection of uninfected wounds.

In one aspect, the invention provides a convenient means for wound care and management and may be used in combination with the apparatus and methods described in U.S. 2010/030132, which is hereby incorporated by reference in its entirety. For example, the method may comprise supplying the stabilized solution to a wound site by one or more of soak, scrub, pulsed lavage, hydrosurgery, and ultrasound to effectively debride and disinfect a wound or tissue. The solution may be delivered before, during and/or after negative pressure wound therapy to promote proper wound healing physiology. In these embodiments, the method may employ a wound dressing for coordinating debridement by infusion of hypochlorous acid with negative pressure therapy. Thus, the invention may be used in combination with a wound treatment apparatus and/or wound dressing.

For example, in certain embodiments, the invention allows for an initial stabilized hypochlorous acid solution soak and/or scrub to both debride and disinfect the wound or tissue, followed by the application of negative pressure to the wound or tissue (as described herein) using the stabilized hypochlorous acid solution as an irrigant to control wound bioburden, remove excess exudate, and promote formation of granulation tissue. Optionally, the method also involves seamless transition to the stabilized hypohalous acid solution infusion (e.g., active or passive infusion without negative pressure). Such seamless transition can be effected via a wound dressing which allows for controlled infusion of stabilized hypochlorous acid solution with controlled vacuum source. In these embodiment, continued cell proliferation and regeneration continues without disruption of the wound bed, once the endpoints of negative pressure therapy have been obtained.

In certain embodiments of the invention, the wound needing care is a stage I-IV pressure ulcer, stasis ulcer, diabetic ulcer, post-surgical wound, burn, cut, abrasion, or a minor irritation of the skin. In certain embodiments, the wound is rinsed, washed, or immersed in the solution periodically over at least two weeks, but treatment may continue periodically for over about 4 weeks, about 9 weeks, or more. The wound, in some embodiments, is rinsed with the solution at least once a week, but may be treated with the solution at least twice a week, or more frequently.

While the hypohalous acid solution may be delivered to the wound at room temperature, the solution may alternatively be heated, for example, to body temperature or about body temperature. In this embodiment, the solution is comfortable and soothing for the patient, and is more effective.

In some embodiments, the invention provides a method for treating an infected or colonized wound, tissue, surgical cavity, or bone, and a method for reducing wound bioburden. The treatment solution in accordance with the invention, as already described, is generally effective for killing or inactivating a broad spectrum of bacterial, fungal, and viral pathogens, including *S. aureus, P. aeruginosa, E. coli, Enterococcus* spp., *C. difficile*, and *Candida* Spp. The solution does not produce resistant species, making the methods desirable over the delivery of traditional antibiotics.

In another aspect, the solution of the invention is particularly suitable for use in conjunction with stem cell and growth factor therapy, including the use of genetically engineered cells and engineered tissue and allografts and organs for transplant in various treatments. Using the stabilized hypohalous acid solution of the invention to disinfect tissue before, during or after addition of cells or growth factors, maintains the viability of the cells and integrity of the growth factors, while killing the unwanted microbes.

In certain embodiments, the solution or formulation thereof is applied for the control of inflammation, including an inflammatory reaction or hyper inflammation of the skin. For example, the solution or formulation thereof may be applied for use in a method as described in US 2007/0196357 or US 2010/0285151, which are hereby incorporated by reference. In certain embodiments, the solution or composition of the invention is applied (e.g., to an effected area) for treatment of a patient having a dermatoses, atopic dermatitis, skin allergy, rosacea, psoriasis, or acne, among others. In such embodiments, the HOCl solution may be formulated as a hydrogel, for example, as described elsewhere herein.

In certain embodiments, invention is advantageous for use against microbes on surfaces because of its fast activity against bacterial spores, fungi, and other resistant microorganisms. Because of its effectiveness and the speed at which it acts, the invention meets a substantial public health need, and one that is not adequately addressed by current commonly-used antimicrobial agents. Accordingly, application of the solution to various surfaces and materials is useful to control microbial contamination, not only for the care and management of wounds, but for disinfecting hard surfaces such as medical or dental equipment, preserving and decontaminating food products, water treatment, as well as other industrial and agricultural applications. In certain embodiments, the solution or composition of the invention is applied to crops (pre- or post-harvest) or cut flowers for their preservation and/or for improving the overall quality of the product. In some embodiments, the solution is potassium based and has one or more utilities (e.g., methods of use) disclosed in PCT/US2011/43590), which is hereby incorporated by reference in its entirety.

In various embodiments, including the treatment of food, agricultural products, and surfaces the solution can be applied as a mist, fog, spray, or ice.

Killing, inactivating, or otherwise reducing the active population of bacterial spores and fungi on surfaces is particularly difficult. Bacterial spores have a unique chemical composition of spore layers that make them more resistant than vegetative bacteria to the antimicrobial effects of chemical and physical agents. Likewise, the unique chemical composition of fungal cells, especially mold spores, makes them more resistant to chemical and physical agents than are other microorganisms. This resistance can be particularly troublesome when the spores or fungi are located on surfaces such as food, food contact sites, ware, hospitals and veterinary facilities, surgical implements, and hospital and surgical linens and garments.

Control of the mold *Chaetomium funicola*, and of bacterial spore-forming microorganisms of the *Bacillus* species, can be especially important during food packaging, particularly during cold or hot aseptic filling of food and beverage products. Microorganisms of the *Bacillus* species include *Bacillus cereus, Bacillus mycoides, Bacillus subtilis, Bacillus anthracis*, and *Bacillus thuringiensis*. These latter microorganisms share many phenotypical properties, have a high level of chromosomal sequence similarity, and are known enterotoxin producers. *Bacillus cereus* is one of the most problematic because *Bacillus cereus* has been identified as possessing increased resistance to germicidal chemicals used to decontaminate environmental surfaces.

As used herein, the term "surface" refers to both hard and soft surfaces and includes, but are not limited to, tile grout, plaster, drywall, ceramic, cement, clay, bricks, stucco, plastic, wallpaper, fabric, tiles, cement, and vinyl flooring, heating and/or cooling fins, filters, vanes, baffles, vents, crevices in walls or ceilings, paper and wood products such as lumber, paper, and cardboard, woven products such as blankets, clothing, carpets, drapery and the like. The term surface also includes human surfaces, animal surfaces, military equipment, transportation equipment, children's items, plant surfaces, seeds, outdoor surfaces, soft surfaces, air, wounds, and medical instruments, and the like.

EXAMPLES

Example 1: Stabilized Hypochlorous Acid Solution

FIGS. 1A and 1B and FIGS. 2A and 2B show five cycles of AFC and pH measurements for hypochlorous acid wound treatment solutions as a function of time under two environmental conditions—COLD (C) and ROOM TEMP (R). As shown, both the pH and AFC content were not stabilized over the long term. For example, the solutions were not stabilized for more than about one week.

In an attempt to stabilize the solution, hypochlorous acid was produced by electrochemical treatment of an electrolyte comprising 4.2 g/L NaCl and 400 mg/L $NaHCO_3$. Samples were buffered with sodium bicarbonate ($NaHCO_3$) at pH 5.6, sodium bicarbonate ($NaHCO_3$) in combination with disodium phosphate ($Na_2HPO_4$) at pH 6.7, or a mix of sodium bicarbonate ($NaHCO_3$), disodium phosphate and sodium diphosphate (9 $NaH_2PO_4$:1$Na_2HPO_4$) at pH 5.6. Solutions were stored in the dark for 1 month in HDPE bottles prior to measuring AFC.

Figure 3:
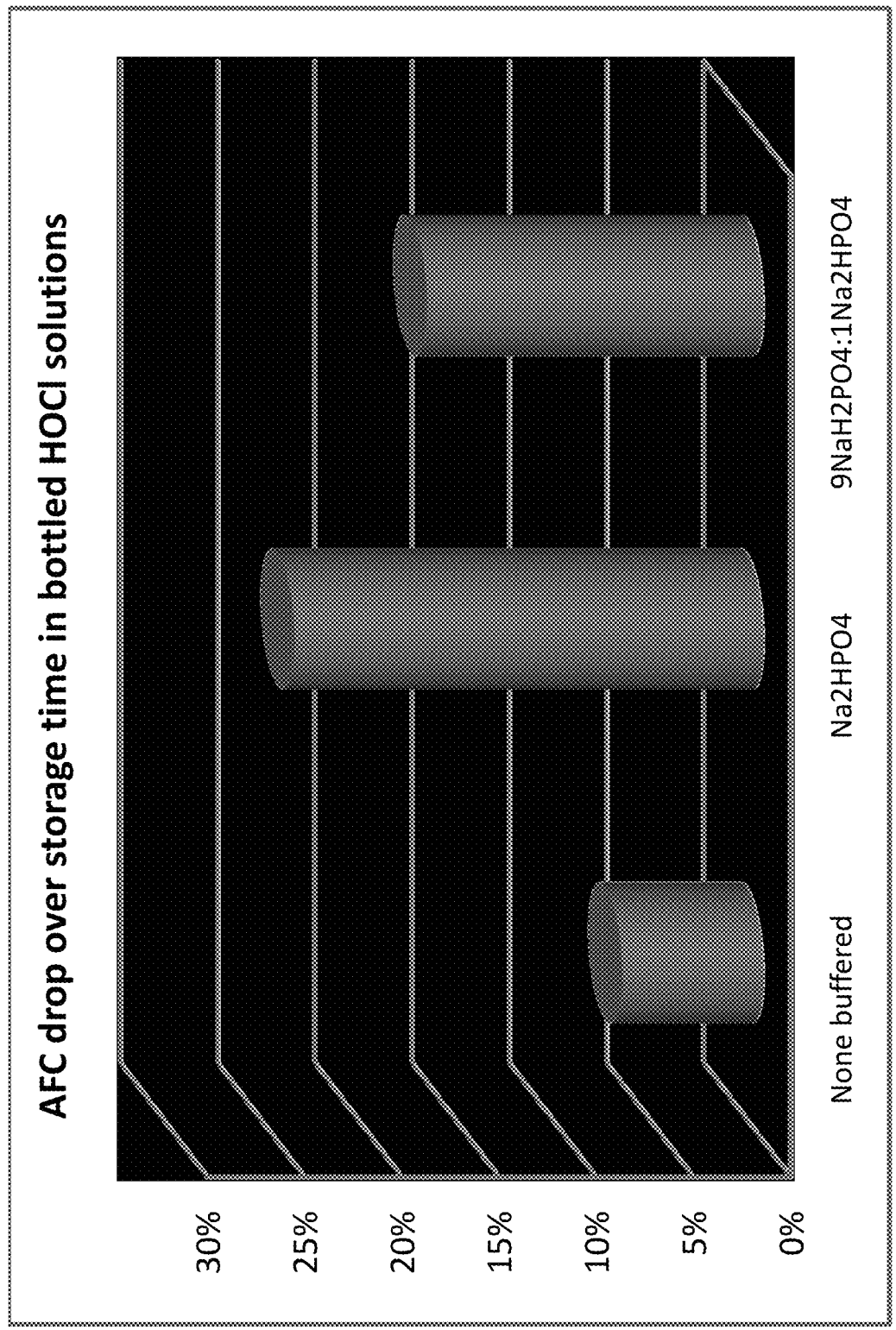
FIG. 3 shows the AFC drop over storage time in bottled HOCl solutions containing bicarbonate ("non-buffered"), or with bicarbonate and phosphate buffer.

FIG. 3 shows the AFC drop as a function of time. The results show that solutions containing no phosphate buffer were considerably more stable (~8% lost) when compared to $Na_2HPO_4$ buffered (~25% lost) and 9 $NaH_2PO_4$:1$Na_2HPO_4$ buffered solutions (~20% lost).

Figure 4:
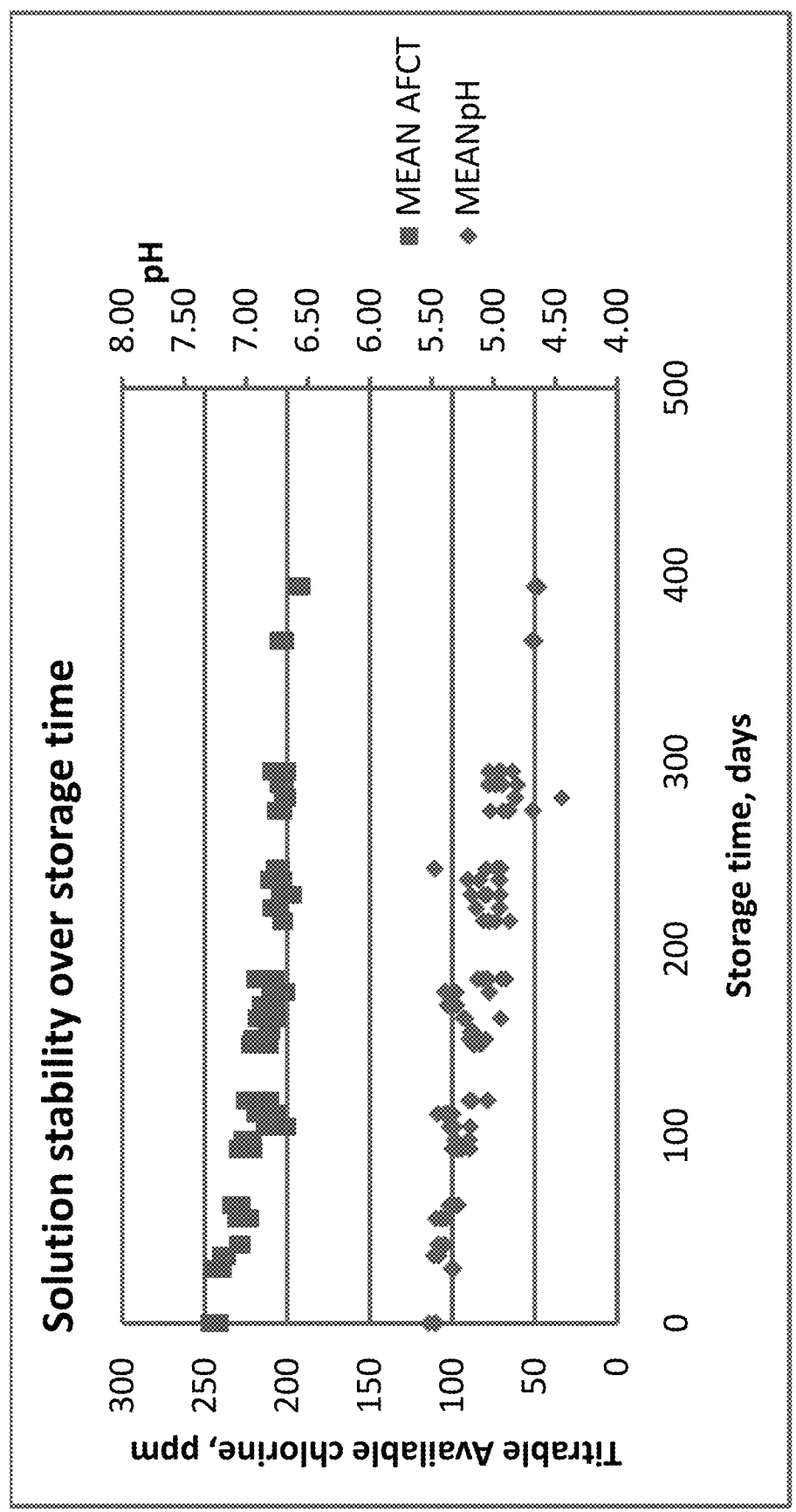
FIG. 4 shows the change in pH and AFC of the bicarbonate-containing HOCl solutions without phosphate buffer.

The stability of the stabilized solution as a function of time was tested. Hypochlorous acid was produced by electrochemical treatment of an electrolyte comprising 4.2 g/L NaCl and 400 mg/L $NaHCO_3$. The solution had a pH of 5.3, an alkalinity of zero (0), and approximately 250 ppm of AFC. This solution was packaged in HDPE bottles and stored in the dark. The biocidal activity and stability of the solution as a function of time was tested by measuring pH and AFC content in unopened test bottles over a period of greater than 390 days. The results are shown in FIG. 4, showing that the solutions are stabilized, with regard to AFC content and pH for over one year.

Generally, it is assumed by NaOCl manufacturers that sodium hypochlorite solution loses approximately 20% of its titrable chlorine in the first 6 months and up to 60% within a year. One study determined that it would take 166 days for a solution of 25 mg/mL sodium hypochlorite solution at 20° C. to reach 20 mg/mL of free residual chlorine based on stability studies conducted at 50° C. and 70° C. and calculations with the Arrhenius Equation (See Nicoletti et al., "Shelf-Life of a 2.5% Sodium Hypochlorite Solution as Determined by Arrhenius Equation," Braz Dent J (2009) 20(1): 27-31). Other studies have shown similar results (See "Product Characteristics, Sodium Hypochlorite-Stability PCH-1400-0007" PCH-1400-0007-W-EN (WW), Issue 1—May 2005, Published by Solvay Chemicals International SA). Contrary to these assumptions, the $NaHCO_3$ buffered hypochlorous acid solution of the claimed invention retained greater than 75% of the initial level of titrable chlorine along with a pH shift of less than one unit over a period of one year.

Example 2: Biocidal Activity of Stabilized HOCl Solution

Three solutions comprising different concentrations of hypochlorous acid were produced. The first solution, containing 250 ppm hypochlorous acid, was produced via electrochemical treatment of an electrolyte comprising 4.2 g/L NaCl and 400 mg/L $NaHCO_3$. The second solution, similarly produced via electrochemical treatment, contained 480 ppm hypochlorous acid, but no $NaHCO_3$. The final solution contained 480 ppm hypochlorous acid, but in addition, incorporated 1000 mg/L $NaHCO_3$.

To simulate a worst-case scenario, spores of C. difficile, a bacterial strain with high antibiotic resistance, were suspended in a highly concentrated organic medium, consisting of homogenized skin cells from pig, mucin, and bovine serum albumin. After suspending the microorganisms in the organic solution, they were inoculated onto plastic carriers, allowed to desiccate and exposed to each solution in duplicate for either 0, 4, 6, 8, 10 or 30 minutes. Due to the fact that none of the existing disinfectants have stood up to this organic load (including bleach), two different concentrations of hypochlorous acid were tested.

The results (FIG. 5) demonstrate that the solution with sodium bicarbonate possesses higher biocidal activity against C. difficile spores under high organic load conditions.

Example 3: Extended Stability Study

Figure 6:
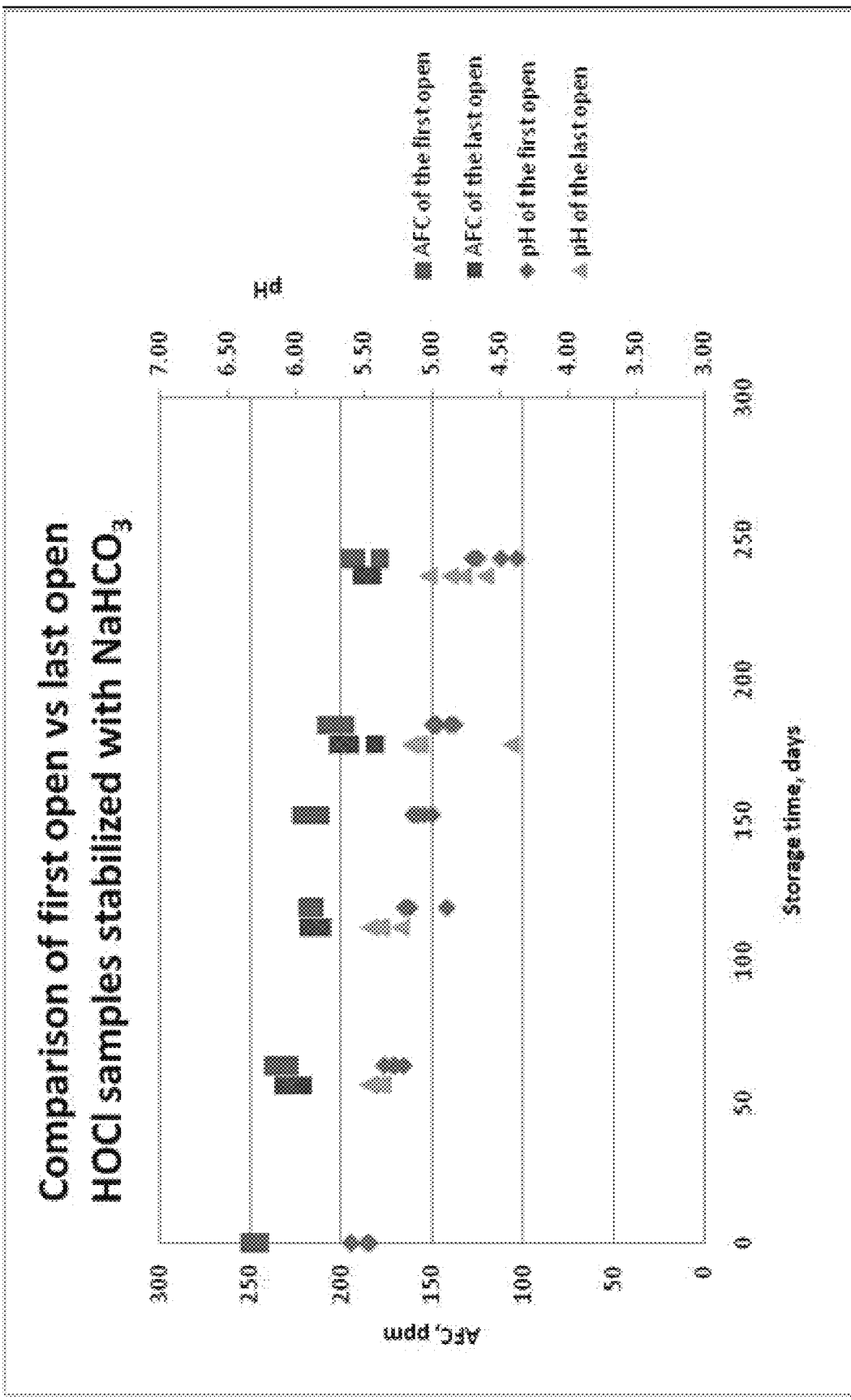
FIG. 6 shows the results of an extended stability study of HOCl produced by electrochemical treatment of $NaHCO_3$-enriched NaCl solution at targeted pH 5.4, bottled in a polyethylene terephthalate (PET) container and stored at room temperature.

FIG. 6 shows the results of an extended stability study of HOCl produced by electrochemical treatment of $NaHCO_3$ enriched NaCl solution at targeted pH 5.4, bottled in a polyethylene terephthalate (PET) container and stored at room temperature. The molar content of $NaHCO_3$ is equivalent to 1 mole $NaHCO_3$ per 1 mole HOCl in this formulation. Every second month 4 new samples of HOCl stabilized solution were opened over the storage time, and then reopened one month later and tested on a weekly basis. Comparison of the pH and AFC of the first opened sample with the last opened, weekly opened during that month, confirmed the stability of HOCl stabilized with sodium bicarbonate.

Example 4: Stability of HOCl with Added Sodium Bicarbonate

Figure 7A:
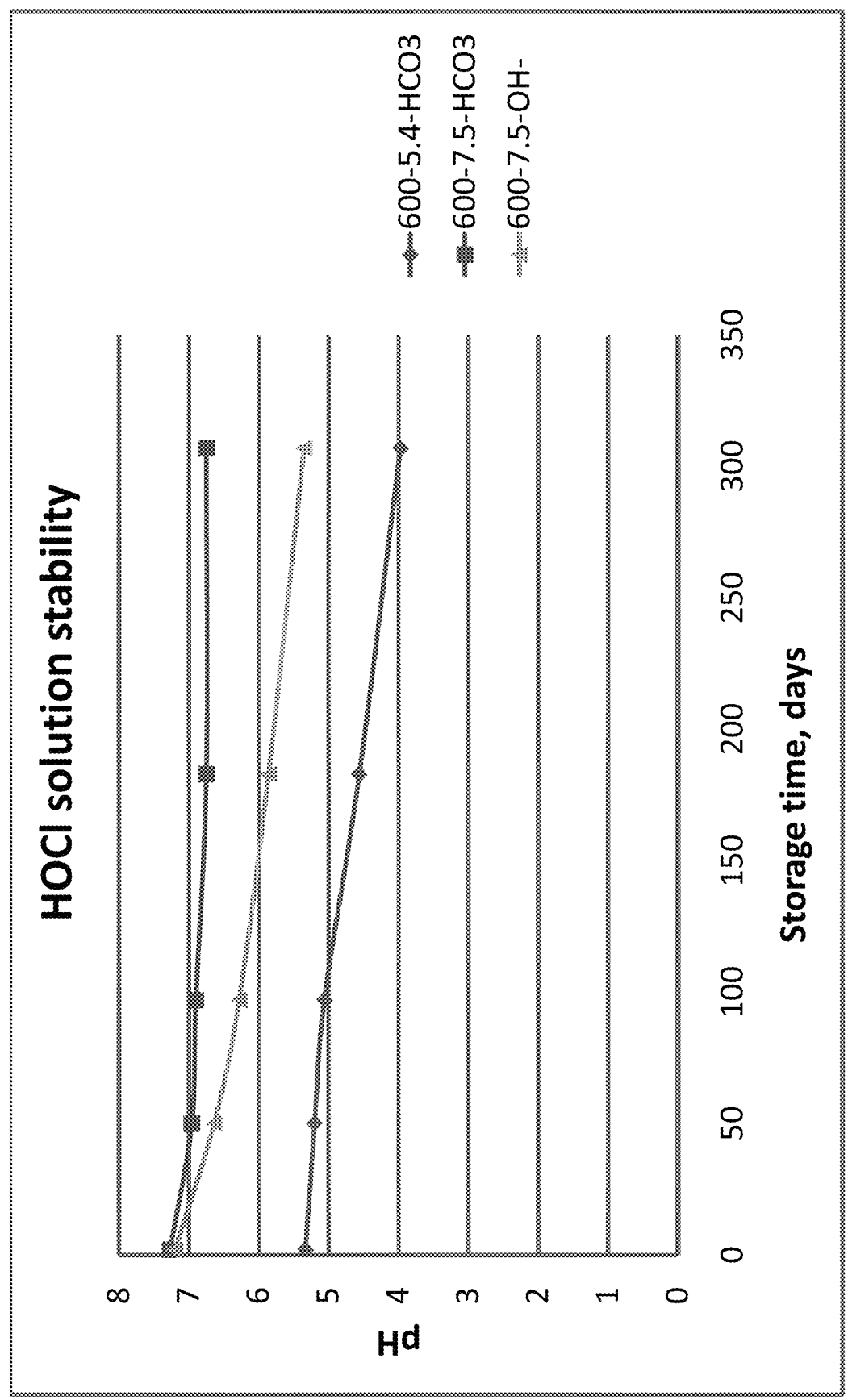
FIGS. 7A and 7B show the stability of HOCl added to containers comprising dry sodium bicarbonate.
Figure 7B:
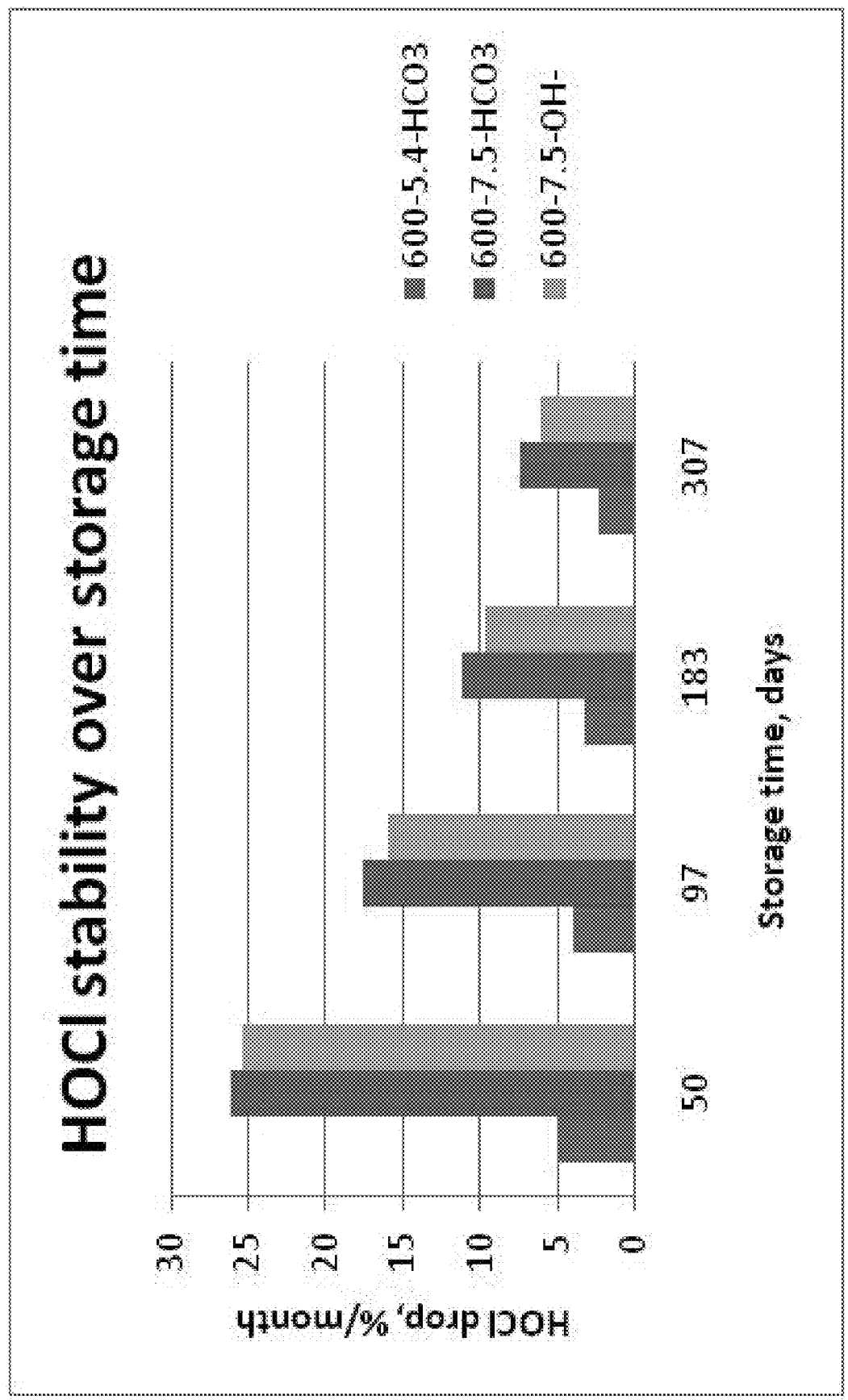

The stability of HOCl added to containers comprising dry sodium bicarbonate is shown in FIGS. 7A and 7B. The ionic strength or solution salinity was not affected by the addition of sodium bicarbonate. The results demonstrate that bicarbonate as a stabilizer affects both the pH and AFC stability. Without being bound to any theory, in cases where the pH is about 5.5 and the buffering ability of bicarbonate is minimal, bicarbonate may act as a stabilizer, in part, by scavenging free radicals generated by the dissociation of hypochlorous acid. The result is a minimal drop in pH and AFC over time.

Example 5: Stability of HOCl Composition for Agricultural Applications

Figure 8:
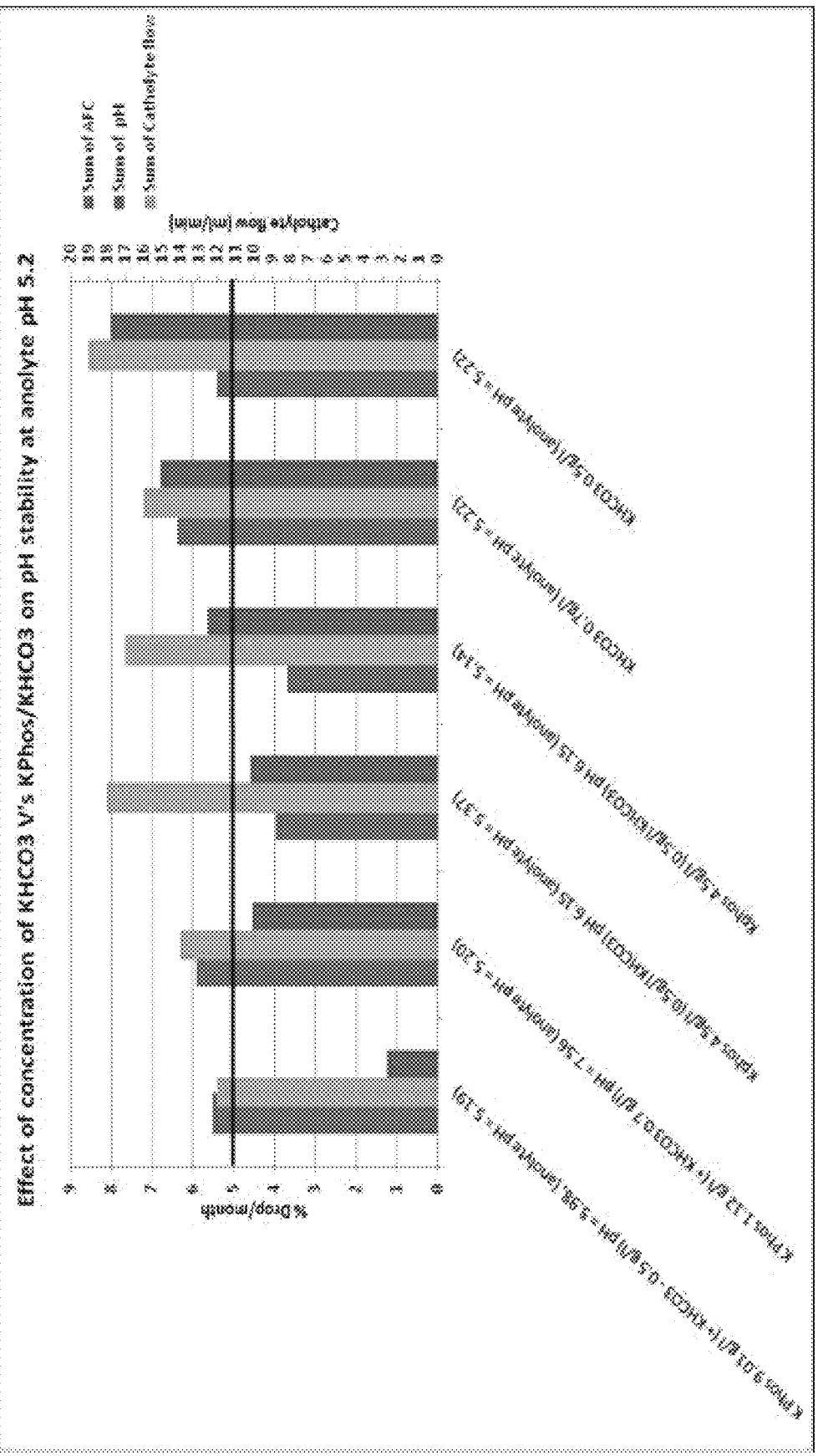
FIG. 8 shows the effect of bicarbonate on pH and solution stability in hypochlorous acid solutions having a targeted pH for agricultural applications.

The effect of DIC content on pH and solution stability in hypochlorous acid solutions electrochemically generated, and additionally buffered with di- and monosodium phosphate for targeted pH (which have utility for agricultural applications), is shown in FIG. 8. Compositions of hypochlorous acid with phosphate additives were tested with and without bicarbonate. The results showed better stability of hypochlorous acid in the presence of bicarbonate than with phosphates alone. Combination of DIC and phosphate buffers provided better solution stability without significantly increasing the total dissolved solids content.

Example 6: Hydrogel Formulations

A hydrogel formulation containing the stabilized hypochlorous acid solution was developed. The use of bicarbonate or dissolved inorganic carbon in accordance with the invention has only a minimal effect on the ionic strength or electroconductivity of the solution. Thus, in addition to stabilizing a HOCl solution in the pH range of about 4 to about 7.5 (e.g. about 6.0), bicarbonate or carbonate do not affect the ionic strength at the targeted pH, making it possible to use hypochlorous acid with more than 200 ppm of available free chlorine as the dispersing media in a gel formulation, especially where low ionic strength is critical for the formulation.

A low ionic strength hypochlorous acid solution (conductivity ≤mS/cm (i.e., millisiemens per centimeter)), AFC=300 ppm, pH 5.3 was used for a hydrogel formulation containing 3% sodium magnesium fluorosilicate. More than 4% sodium magnesium fluorosilicate was required for the production of a hydrogel of equal viscosity made out of 8 mS/cm of HOCl with equal pH and AFC content. A lower ionic strength HOCl solution as a dispersing media allows for the addition of other buffering agents for pH optimization in the final product without negative effects on physical appearance and product stability. Due to the fact that the gelling agent is a dry buffer itself, the ability to add other buffers for pH optimization in a final product can be beneficial.

Figure 9:
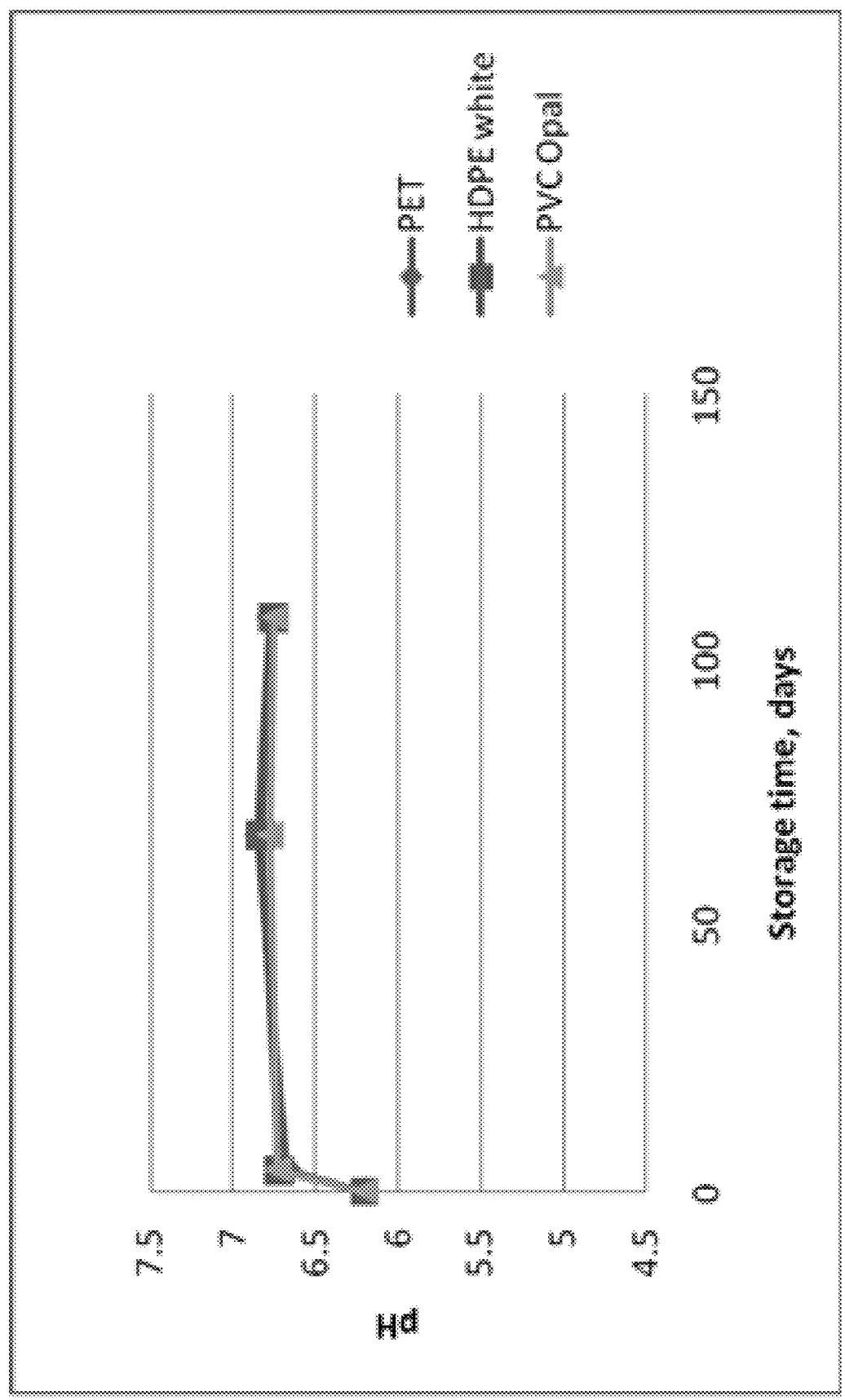
FIG. 9 shows a shift in pH upon formulation as a hydrogel.

In another example, hypochlorous acid solution, AFC 350 ppm, pH 5.3, salinity 4 g/l (conductivity 8 mS/cm) was used for the production of a hydrogel containing 4% $F_{12}MgNa_2Si_2$ (sodium magnesium fluorosilicate). The hydrogel produced had a viscosity of 330 centipoises (cP) and a pH of 8.2. To bring the pH to a "skin-friendly" range phosphoric acid was added as a buffering agent. The final hydrogel had a shift in pH over time from pH 6 to 6.8 as seen in FIG. 9. Additional buffer is limited by gel viscosity as it shifts to 220 cP with a conductivity increase to 10 mS/cm.

Low ionic strength hypochlorous acid, AFC=370 ppm, was produced by electrochemical treatment of sodium chloride substantially as described in U.S. Pat. No. 7,897,023 (which is hereby incorporated by reference in its entirety), and collected in a container with dry sodium bicarbonate, equivalent to 500 ppm of $NaHCO_3$ as an initial form of dissolved inorganic carbon (DIC). An HOCl pH 5.2 and conductivity 0.8 mS/cm produced by this process was and used as dispersing media for a gel preparation. 3% of sodium magnesium fluorosilicate was used as a gelling agent. Hydrogel formed with a viscosity of about 10,000 cP in less than 25 minutes with an initial pH of 8.4 and a conductivity of about 1 mS/cm. Phosphoric acid was added in the amount of less than 0.25% to bring the pH of the hydrogel down to a skin-friendly range (about pH 5.5-5.8). A hydrogel with a viscosity above 2,000 cP was formed.

All references cited herein are incorporated by reference in their entireties.

What is claimed is:

1. A stabilized hypobromous acid (HOBr) solution consisting of:
    a solution prepared by electrolysis of a solution consisting of water, a bromide salt, and optionally dissolved inorganic carbon (DIC) in the form of bicarbonate or carbonate of alkali or alkaline earth metals, and
    a stabilizing amount of DIC in the form of bicarbonate or carbonate of alkali or alkaline earth metals, wherein an available free bromine (AFB) content of the solution is from about 10 to about 5,000 parts per million (ppm), wherein the pH of the solution is from 4.0 to 7.5, and wherein a ratio of the stabilizing amount of the DIC to the AFB content is at least 1:2.

2. The solution of claim 1, wherein the AFB content and the pH of the solution are stable for at least 6 months.

3. The solution of claim 1, wherein the AFB content is from about 100 to about 1,000 ppm, from about 100 to about 500 ppm, or from about 150 to about 250 ppm.

4. The solution of claim 1, wherein the pH is from 5.0 to 7.0.

5. The solution of claim 1, wherein the pH is from 5.0 to 6.4.

6. The solution of claim 1, wherein the DIC is sodium bicarbonate.

7. The solution of claim 1, wherein the stabilized solution has an AFB content of from 100 ppm to 500 ppm and from 300 mg/L to 1000 mg/L of sodium bicarbonate.

8. A method for disinfecting or cleansing a mammalian tissue, comprising applying the solution of claim 1 to the mammalian tissue.

9. The method of claim 8, wherein the mammalian tissue is infected, has a wound or a burn, has a dermatosis, or has atopic dermatitis.

10. A method for disinfecting or cleansing a hard surface, comprising applying the solution of claim 1 to the hard surface.

11. The method of claim 10, wherein the hard surface comprises porcelain, steel, iron, or ceramic material.

12. A method for preserving or decontaminating food products, comprising applying the solution of claim 1 to a food product.

13. A method for controlling microbial contamination of water, comprising applying the solution of claim 1 to water in need of treatment or control for microbial contamination.

\* \* \* \* \*